United States Patent [19]
Ichihara et al.

[11] Patent Number: 5,900,486
[45] Date of Patent: May 4, 1999

[54] N-BENZYLAZOLIUM DERIVATIVES

[75] Inventors: Shigeyasu Ichihara; Chikako Murasaki, both of Kamakura; Noriko Ohga, Yokohama; Jun Ohwada, Kamakura; Daisuke Sawada, Tokyo-to; Nobuo Shimma, Chigasaki, all of Japan; Michio Shirai, Chicago, Ill.; Isao Umeda, Yokohama, Japan

[73] Assignee: Hoffmann-La Roche Inc., Nutley, N.J.

[21] Appl. No.: 08/926,392

[22] Filed: Sep. 9, 1997

[30] Foreign Application Priority Data

Sep. 9, 1996 [EP] European Pat. Off. ............. 96114390
Aug. 18, 1997 [EP] European Pat. Off. ............. 97114246

[51] Int. Cl.[6] ................................................ C07D 417/06
[52] U.S. Cl. .................... 548/204; 514/365; 514/252; 546/270.4; 548/205; 548/117; 548/263.2; 548/266.2; 548/341.1; 544/238; 544/365; 544/366; 544/370
[58] Field of Search .................... 548/204, 205; 514/365

[56] References Cited

U.S. PATENT DOCUMENTS

| | | | |
|---|---|---|---|
| 4,017,631 | 4/1977 | Janssen. | |
| 4,243,670 | 1/1981 | Regel. | |
| 4,251,540 | 2/1981 | Regel et al.. | |
| 4,267,179 | 5/1981 | Heeres | 544/366 |
| 4,404,216 | 9/1983 | Richardson | 549/563 |
| 4,497,819 | 2/1985 | Rentzea | 514/397 |
| 4,861,879 | 8/1989 | Heeres | 544/55 |
| 5,128,351 | 7/1992 | Wissner | 514/365 |
| 5,648,372 | 7/1997 | Naito et al. | 514/365 |

FOREIGN PATENT DOCUMENTS

| | | |
|---|---|---|
| 0 130 366 | 1/1985 | European Pat. Off.. |
| 130 366 | 1/1985 | European Pat. Off.. |
| 667 346 A2 | 8/1995 | European Pat. Off.. |
| 1519132 | 3/1968 | France. |
| 1 519 132 | 7/1968 | France. |
| 2 486 079 | 1/1982 | France. |
| 8015323 | 1/1982 | France. |
| 2 531 031 | 1/1977 | Germany. |
| 3 217 963 | 11/1983 | Germany. |

OTHER PUBLICATIONS

Wang, Z., et al., *Progress in Natural Science*, 2(6):505–511 (Dec., 1992).
Derwent Abstract No. 1784969. (1977.
Derwent Abstract No. 4162120. (1985).
Derwent Abstract No. 541788. (1968).
Derwent Abstract No. 3464286. (1982).

*Primary Examiner*—Donald G. Daus
*Attorney, Agent, or Firm*—George W. Johnston; William H. Epstein; John P. Parise

[57] ABSTRACT

N-Benzylazolium derivatives of the general formula (I),

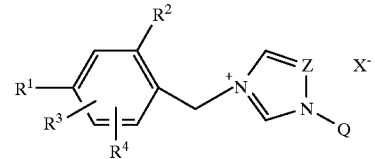

(I)

wherein

Q is the remainder of an azole compound of the formula II

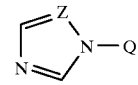

(II)

possessing antifungal activity;

Z is nitrogen or methine;

$R^1$ and $R^2$ are each independently a hydrogen atom or a group —OY [in which Y is a group easily hydrolyzable under physiological condition];

$R^3$ and $R^4$ are each independently a hydrogen or halogen atom, lower alkyl, lower alkoxy, lower alkylthio, (lower alkylcarbonyl)thiomethyl, carboxy or methoxycarbonyl; and $X^-$ is a pharmaceutically acceptable anion, as well as salts, hydrates or solvates of the compounds of the general formula (I) have antifungal properties.

20 Claims, No Drawings

N-BENZYLAZOLIUM DERIVATIVES

BACKGROUND OF THE INVENTION

The present invention relates to novel azole compounds, processes for their manufacture, and antifungal compositions containing said azole compounds.

Although several azole compounds are currently used for systemic mycoses, none of them fulfills the necessary clinical requirement in full extent, i.e. efficacy against major systemic mycoses including disseminated aspergillosis, safety, and oral or parenteral formulations. Particularly, demand of a parenteral administration of the azole compounds is increasing for the treatment of serious systemic mycoses. Most of the azole compounds on the market as well as under development are highly lipophilic molecules that make the parenteral formulation difficult.

SUMMARY OF THE INVENTION

The present invention relates to novel water soluble azole compounds useful for the treatment of systemic mycoses and suitable for both oral and particularly parenteral administration, processes for their manufacture, antifungal compositions containing them and a method for treating mycoses having the general formulas (I) and (I'):

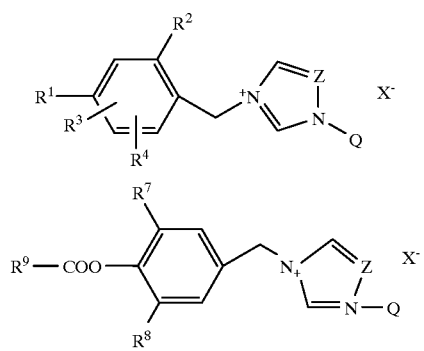

DETAILED DESCRIPTION OF THE INVENTION

The term "lower alkyl" as used in this specification refers to a straight or branched chain having preferably 1 to 4 carbon atoms such as methyl, ethyl, n-propyl, iso-propyl, butyl, iso-butyl or tert-butyl.

The term "lower alkoxy" as used in this specification refers to straight or branched chain having preferably 1 to 4 carbon atoms such as methoxy, ethoxy, n-propoxy, iso-propoxy, n-butoxy, iso-butoxy.

The term "aryl" as used in this specification refers preferably to an unsubstituted or substituted aryl radical such as phenyl, methoxyphenyl, pyridyl, pyrazinyl or furyl.

The term "halogen" as used in this specification denotes preferably fluorine, chlorine or bromine.

The term "lower alkylthio" as used in this specification refers to straight or branched chain having preferably 1 to 4 carbon atoms such as methylthio, ethylthio, n-propylthio.

The novel azole compounds of the present invention have the general formula (I),

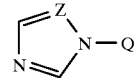

wherein

Q is the remainder of an azole compound of the formula II

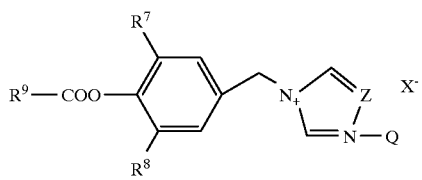

possessing antifungal activity;

Z is nitrogen or methine;

$R^1$ and $R^2$ are each independently a hydrogen atom or a group —OY [in which Y is a group easily hydrolyzable under physiological condition];

$R^3$ and $R^4$ are each independently a hydrogen or halogen atom, lower alkyl, lower alkoxy, lower alkylthio, (lower alkylcarbonyl)thiomethyl, carboxy or methoxycarbonyl; and $X^-$ is a pharmaceutically acceptable anion, as well as pharmaceutically acceptable salts of said compounds, and hydrates and solvates of the compounds of formula I and the salts thereof.

Particularly preferred among the above azole compounds of formula I are those of formula (I'),

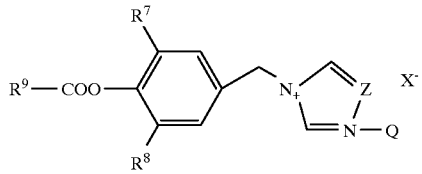

wherein, $R^9$ is a straight-chain or branched $C_1$-$C_5$ alkyl, aryl, pyridyl, pyrrolidinyl or a group A—NH—B— (wherein A is a hydrogen atom or a straight-chain or branched $C_1$-$C_5$ alkyl; B is a straight-chain or branched $C_1$-$C_4$ alkylene, —$CH_2$—CONH—$CH_2$— or —$CH_2CH_2CH_2$—CH($NH_2$)—);

$R^7$ and $R^8$ are each independently a hydrogen or halogen atom or a lower alkoxy;

Z is nitrogen or methine;

$X^-$ is a pharmaceutically acceptable anion; and

Q is the remainder of an azole compound of the formula II

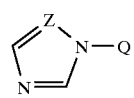

The respective groups in the general formulas (I) and (I') which are defined above are explained in more detail as follows:

The Example of azole compounds of the formula II $$\text{(II)}$$

(structure with Z, N, N—Q)

are dl-1-[2-(2,4-dichlorophenyl)-2-[(2,4-dichlorophenyl)methoxy]ethyl]-1H-imidazole, dl-cis-1-acetyl-4-[4-[2-(2,4-dichlorophenyl)-2-(imidazol-1-ylmethyl)-1,3-dioxolan-4-yl]methoxy]phenyl]piperazine, dl-2-[(RS)-sec-butyl]-4-[4-[4-[(2R,4S)-2-(2,4-dichlorophenyl)-2-(1H-1,2,4-triazol-1-ylmethyl)-1,3-dioxolan-4-yl]methoxy]phenyl]-1-piperazinyl]phenyl]-3H-[1,2,4]triazol-3-one 2-[(1 R,2R)-2-(2,4-diflorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol, (2R)-2-(2,4-difluorophenyl)-1-[3-[(E)-4-(2,2,3,3-tetrafluoropropoxy)-styryl]-(1,2,4-triazol-1-yl)-3-(1,2,4-triazol-1-yl)]propan-2-ol dl-threo-2-(2,4-difluorophenyl)-3-methyl-sulfonyl-1-(1H-1,2,4-triazol-1-yl)-butan-2-ol, (−)-4-[4-[4-[[5-(2,4-difluorophenyl)-5-(1H-1,2,4-triazol-1-ylmethyl)tetrahydrofuran-3-yl]methoxy]phenyl]piperazinyl]phenyl]-2-[(1S,2S)-1-ethyl-2-hydroxypropyl]-3H-1,2,4-triazol-3-one (2R,3R)-3-[4-(4-cyanophenyl)thiazol-2-yl)]-2-(2,4-difluorophenyl)-1-(1H-1,2,4-triazol-1-yl)-butan-2-ol, 3-methyl-3-methylthio-1-(1,2,4-triazol-1-yl)-2-(trifluoromethylphenyl)-butan-2-ol, 1-[[(1 R,2S,6R)-2-methoxy-3,3-dimethyl-6-(2-p-tolylethyl)cyclohexyl]-methyl]-1H-[1,2,4]triazol, (5R,6R)-2,2-dimethyl-6-[(1H-1,2,4-triazol-1-yl)methyl]-5-[[4-(trifluoromethoxy)-phenoxy]methyl]cyclohexanone O-methyloxime, and the like.

Especially preferred among the above azole compounds of formulas I and I' are those wherein Q is the group of the formula,

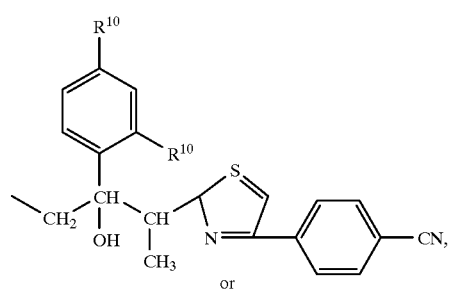

(Q¹)

or

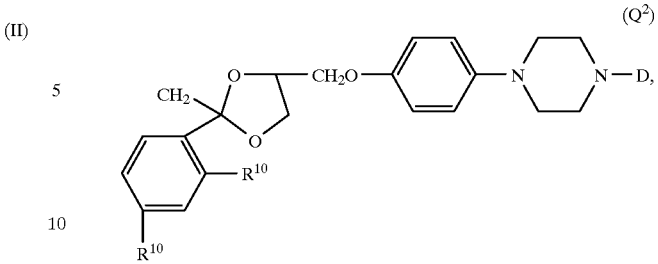

(Q²)

wherein,

D is a lower alkanoyl or the group of the formula,

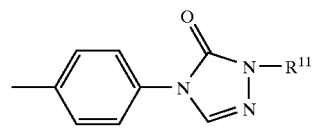

$R^{10}$ is a halogen atom; and $R^{11}$ is a straight-chain or branched $C_1$–$C_4$ alkyl.

$R^1$ and $R^2$ are each independently a hydrogen atom or a group —OY [in which Y is an easily hydrolyzable radical under physiological condition].

In the above a group Y which is easily hydrolyzable under physiological condition means preferably the acyl residue of an amino acid or a group represented by the formula, $R^5CO—$, or $(R^6O)_2PO—$ wherein $R^5$ is hydrogen, lower alkoxy, lower alkyl which may be optionally substituted with carboxyl, amino, lower alkyl amino, dilower alkyl amino, or aryl; and $R^6$ is hydrogen or lower alkyl.

Preferably, Y is selected from the group consisting of formyl, acetyl, propionyl, isobutyryl, pivaloyl, succinoyl, benzoyl, nicotinoyl, phosphoryl, dimethylphosphoryl, aminoacetyl, 3-aminopropionyl, 4-aminobutyryl, (2-aminoacetylamino)-acetyl, (S)-2,5-diaminopentoyl, (S)-2-aminopropionyl, (S)-pyrrolidine-2-carbonyl, (methylamino)acetyl, (propylamino)acetyl, (S)-2-(methylamino)propionyl, 3-(methylamino)propionyl, (S)-2-amino-3-methylbutanoyl, (isopropylamino)acetyl, (2S)-2-(ethylamino)propionyl, (ethylamino)acetyl and the like.

$R^3$ and $R^4$ are each independently a hydrogen or halogen atom, lower alkyl, lower alkoxy, lower alkylthio, (lower alkylcarbonyl)thiomethyl, carboxy or methoxycarbonyl. Preferably, $R^3$ and $R^4$ are independently methyl, methoxy, or chlorine.

Preferably, $R^7$ and $R^8$ are each independently a hydrogen or halogen atom or a lower alkoxy.

Preferably, $R^9$ is a straight-chain or branched $C_1$–$C_5$ alkyl, aryl, pyridyl, pyrrolidinyl or a group A—NH—B— (wherein A is a hydrogen atom or a straight-chain or branched $C_1$–$C_5$ alkyl; B is a straight-chain or branched $C_1$–$C_4$ alkylene, —CH$_2$—CONH—CH$_2$— or —CH$_2$CH$_2$CH$_2$—CH(NH$_2$)—).

$X^-$ is an anion from a pharmaceutically acceptable inorganic acid, e.g. a mineral acid; such as chloride, bromide or sulfate; or from an organic acid, e.g. an aliphatic, aromatic or araliphatic carboxylic or sulfonic acid such as acetoxy, trifluoroacetoxy, mesyloxy anion and the like.

Particularly preferred compounds in accordance with the present invention are:

dl-1-(4-acetoxy-3,5-dimethylbenzyl)-3-[2-(2,4-dichlorobenzyloxy)-2-(2,4-dichlorophenyl)ethyl]-3H-imidazol-1-ium bromide, dl-1-(4-acetoxy-3-methylbenzyl)-3-[2-(2,4-dichlorobenzyloxy)-2-(2,4-dichlorophenyl)ethyl]-3H-imidazol-1-ium bromide, dl-1-(4-acetoxybenzyl)-3-[2-(2,4-dichlorobenzyloxy)-2-(2,4-dichlorophenyl)ethyl]-3H-imidazol-1-ium bromide, dl-1-(4-acetoxybenzyl)-3-[(2R,4S)-4-[4-(4-acetylpiperazin-1-yl)phenoxymethyl]-2-(2,4-dichlorophenyl)-[1,3]dioxan-2-ylmethyl]-3H-imidazol-1-ium bromide, dl-1-(4-acetoxy-3,5-dimethylbenzyl)-3-[(2R,4S)-4-[4-(4-acetylpiperazin-1-yl)phenoxymethyl]-2-(2,4-dichlorophenyl)-[1,3]dioxan-2-ylmethyl]-3H-imidazol-1-ium bromide, dl-1-(4-acetoxy-3-methylbenzyl)-3-[(2R,4S)-4-[4-(4-acetylpiperazin-1-yl)phenoxymethyl]-2-(2,4-dichlorophenyl)-[1,3]dioxan-2-ylmethyl]-3H-imidazol-1-ium bromide, dl-1-(4-acetoxy-3-methoxybenzyl)-3-[(2R,4S)-4-[4-(4-acetylpiperazin-1-yl)phenoxymethyl]-2-(2,4-dichlorophenyl)-[1,3]dioxan-2-ylmethyl]-3H-imidazol-1-ium bromide, dl-3-[(2R,4S)-4-[4-(4-acetylpiperazin-1-yl)phenoxymethyl]-2-(2,4-dichlorophenyl)-[1,3]dioxan-2-ylmethyl]-1-(4-isobutyryloxy-3,5-dimethylbenzyl)-3H-imidazol-1-ium bromide, dl-3-[(2R,4S)-4-[4-(4-acetylpiperazin-1-yl)phenoxymethyl]-2-(2,4-dichlorophenyl)-[1,3]dioxan-2-ylmethyl]-1-(4-pivaloyloxy-3,5-dimethylbenzyl)-3H-imidazol-1-ium bromide, dl-3-[(2R,4S)-4-[4-(4-acetylpiperazin-1-yl)phenoxymethyl]-2-(2,4-dichlorophenyl)-[1,3]dioxan-2-ylmethyl]-1-[4-(2,2-dimethylpropionyloxy)benzyl]-3H-imidazol-1-ium bromide, dl-4-(4-benzoyloxy-3,5-dimethylbenzyl)-1-[4-[4-[4-(1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium bromide, dl-4-[4-(pyridine-3-carbonyloxy)-3,5-dimethylbenzyl]-1-[4-[4-[4-(1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium bromide, dl-4-(4-acetoxy-3,5-dimethylbenzyl)-1-[4-[4-[4-[1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium bromide, dl-4-(4-acetoxy-3-methylbenzyl)-1-[4-[4-[4-[1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium bromide, dl-4-(4-acetoxybenzyl)-1-[4-[4-[4-[1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium bromide, dl-1-[4-(4-{4-[4-(1-sec-butyl-5-oxo-1,5-dihydro-[1,2,4]triazol-4-yl)-phenyl]-piperazin-1-yl}-phenoxymethyl)-2-(2,4-dichloro-phenyl)-[1,3]dioxolan-2-ylmethyl]-4-(4-hexanoyloxy-3,5-dimethylbenzyl)-1H-[1,2,4]triazol-4-ium methanesulfonate, 4-(4-acetoxy-3,5-dimethylbenzyl)-1-[(2R,3R)-2-(2,4-difluorophenyl)-2-hydroxy-3-{5-oxo-4-[4-(2,2,3,3-tetrafluoropropoxy)phenyl]-4,5-dihydro-[1,2,4]triazol-1-yl}butyl]-1H-[1,2,4]triazol-4-ium bromide, 4-(4-acetoxy-3,5-dimethylbenzyl)-1-[(2R)-2-(2,4-difluorophenyl)-2-hydroxy-3-methyl-3-(6-[1,2,4]triazol-1-yl-pyridazin-3-ylsulfanyl)butyl]-1H-[1,2,4]triazol-4-ium bromide, 4-(4-acetoxy-3,5-dimethylbenzyl)-1-[(2R)-2-(2,4-difluorophenyl)-2-hydroxy-3-(3-{(Z)-2-[4-(2,2,3,3-tetrafluoropropoxy)phenyl]vinyl}-[1,2,4]triazol-1-yl)propyl]-1H-[1,2,4]triazol-4-ium bromide, 4-(4-acetoxy-3,5-dimethylbenzyl)-1-[(2R,3R)-2-(2,4-difluorophenyl)-2-hydroxy-3-methanesulfonylbutyl]-1H-[1,2,4]triazol-4-ium bromide, 4-(4-acetoxy-3,5-dimethylbenzyl)-1-[(2R-cis)-2-(2,4-difluorophenyl)-4-[4-[4-[4-[1-[(1S,2S)-1-ethyl-2-hydroxypropyl]-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxy-3-methylbenzyl)-1-[(2R-cis)-2-(2,4-difluorophenyl)-4-[4-[4-[4-[1-[(1S,2S)-1-ethyl-2-hydroxypropyl]-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxybenzyl)-1-[(2R-cis)-2-(2,4-difluorophenyl)-4-[4-[4-[4-[1-[(1S,2S)-1-ethyl-2-hydroxypropyl]-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxy-3,5-dichlorobenzyl)-1-[(2R-cis)-2-(2,4-difluorophenyl)-4-[4-[4-[4-[1-[(1S,2S)-1-ethyl-2-hydroxypropyl]-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxy-3-chlorobenzyl)-1-[(2R-cis)-2-(2,4-difluorophenyl)-4-[4-[4-[4-[1-[(1S,2S)-1-(ethyl-2-hydroxypropyl)]-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxy-3,5-dimethylbenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxy-3-methylbenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxybenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxy-3,5-dichlorobenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxy-3-chlorobenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, (2R,3R)-4-(4-aminoacetoxy-2-carboxybenzyl)-1-[3-[4-(4-cyano-phenyl)-thiazol-2-yl]-2-(2,4-difluorophenyl)-2-hydroxybutyl]-1H-[1,2,4]triazol-4-ium bromide trifluoroacetic acid salt, 1-[(2R,3R)-3-[4-(4-cyanophenyl)-thiazol-2-yl]-2-(2,4-difluorophenyl)-2-hydroxybutyl]-4-[(S)-3,5-dimethyl-4-(pyrrolidine-2-carbonyloxy)-benzyl]-1H-[1,2,4]triazol-4-ium bromide trifluoroacetic acid salt, (2R,3R)-4-(4-aminoacetoxy-3,5-dimethylbenzyl)-1-[3-[4-(4-cyano-phenyl)-thiazol-2-yl]-2-(2,4-difluorophenyl)-2-hydroxybutyl]-1H-[1,2,4]triazol-4-ium bromide trifluoroacetic acid salt, (2R,3R)-4-[4-(3-aminopropionyloxy)-3,5-dimethylbenzyl]-1-[4-[4-(4-cyanophenyl)-thiazol-2-yl]-2-(2,4-difluorophenyl)-2-hydroxy-3-methylbutyl]-1H-[1,2,4]triazol-4-ium bromide trifluoroacetic acid salt, (2R,3R)-4-[4-(4-amino-butyryloxy)-3,5-dimethylbenzyl]-1-[4-[4-(4-cyano-phenyl)-thiazol-2-yl]-2-(2,4-difluorophenyl)-2-hydroxy-3-methylbutyl]-1H-[1,2,4]triazol-4-ium bromide trifluoroacetic acid salt, (2R,3R)-4-[4-[[2-(aminoacetyl)amino]acetoxy]-3,5-dimethylbenzyl]-1-[3-[4-(4-cyanophenyl)-thiazol-2-yl]-2-(2,4-difluorophenyl)-2-hydroxy-butyl]-1H-[1,2,4]triazol-4-ium bromide trifluoroacetic acid salt, 1-[(2R,3R)-3-[4-(4-cyanophenyl)-thiazol-2-yl]-2-(2,4-difluorophenyl)-2-hydroxybutyl]-4-[4-[(S)-2,5-diaminopentoyloxy]-3,5-dimethyl-benzyl I-i H-I 1,2,4]triazol-4-ium bromide trifluoroacetic acid salt, 4-[4-[(S )-2-amino-propionyloxy]-3,5-dimethylbenzyl]-1-[(2R,3R)-3-[4-(4-cyanophenyl)-thiazol-2-yl]-2-(2,4-difluorophenyl)-2-hydroxy-butyl]-1H-[1,2,4]triazol-4-ium bromide trifluoroacetic acid salt, 1-[(2R,3R)-3-[4-(4-cyanophenyl)-thiazol-2-yl]-2-(2,4-difluorophenyl)-2-hydroxybutyl]-4-[3,5-dimethyl-4-[(methylamino)acetoxy]benzyl]-1H-[1,2,4]triazol-4-ium bromide trifluoroacetic acid salt, (2R,3R)-1-[3-[4-(4-cyanophenyl)-thiazol-2-yl]-2-(2,4-difluorophenyl)-2-hydroxybutyl]-4-[3,5-dimethyl-4-[(propylamino)acetoxy]benzyl]-1H-[1,2,4]triazol-4-ium bromide trifluoroacetic acid salt, 1-[(2R,3R)-3-[4-(4-cyanophenyl)-thiazol-2-yl]-2-(2,4-difluorophenyl)-2-hydroxybutyl]-4-[4-[(S)-2-(methylamino)propionyloxy]-3,5-dimethyl-benzyl]-1H-[1,2,4]triazol-4-ium bromide trifluoroacetic acid salt, (2R,3R)-1-[4-[4-(4-cyanophenyl)-thiazol-2-yl]-2-(2,4-difluorophenyl)-2-hydroxy-3-methyl-butyl]-4-[3,5-dimethyl-4-[3-(methylamino)-propionyloxy]benzyl]-1H-[1,2,4]triazol-4-ium bromide trifluoroacetate, 4-[4-[(S)-2-amino-3-methyl-butanoyloxy]-3,5-dimethylbenzyl]-1-[(2R,3R)-3-[4-(4-cyanophenyl)-thiazol-2-yl]-2-(2,4-difluorophenyl)-2-hydroxybutyl]-1H-[1,2,4]triazol-4-ium bromide trifluoroacetic acid salt, (2R,3R)-1-[3-[4-(4-cyanophenyl)-thiazol-2-yl]-2-(2,4-difluorophenyl)-2-hydroxybutyl]-4-[4-[(isopropylamino)acetoxy]-3,5-dimethylbenzyl]-1H-[1,2,4]triazol-4-ium bromide trifluoroacetic acid salt, 1-[(2R,3R)-3-[4-(4-cyanophenyl)-thiazol-2-yl]-2-(2,4-difluorophenyl)-2-hydroxybutyl]-4-[(2S)-4-[2-(ethylamino)propionyloxy]-3,5-dimethyl-benzyl]-1H-[1,2,4]triazol-4-ium bromide trifluoroacetic acid salt, (2R,3R)-1-[3-[4-(4-cyanophenyl)-thiazol-2-yl]-2-(2,4-difluorophenyl)-2-hydroxybutyl]-4-[4-[(ethylamino)acetoxy]-3,5-dimethylbenzyl]-1H-[1,2,4]triazol-4-ium bromide trifluoroacetic acid salt 4-(4-acetoxy-3,5-dimethylbenzyl)-1-[2-hydroxy-3-methyl-3-methylsulfanyl-2-(4-trifluoromethylphenyl)butyl]-1H-[1,2,4]triazol-4-ium bromide, 4-(4-acetoxy-3,5-dimethylbenzyl)-1-[[(1 R,6R)-2-methoxyimino-3,3-dimethyl-6-[(4-trifluoromethoxyphenoxy)methyl]cyclohexyl]methyl]-1H-[1,2,4]triazol-4-ium bromide, 4-(4-acetoxy-3,5-dimethylbenzyl)-1-[(1R,2S,6R)-2-methoxy-3,3-dimethyl-6-(2-p-tolyl-ethyl)cyclohexylmethyl]-1H-[1,2,4]triazol-4-ium bromide, 1-[2R,3R)-3-[4-(4-cyano-phenyl)-thiazol-2-yl]-2-(2,4-difluoro-phenyl)-2-hydroxybutyl]-4-(3,5-dimethyl-4-methylaminoacetoxy-benzyl)-1H-[1,2,4]triazol-4-ium bromide hydrochloric acid salt, 1-[2R,3R)-3-[4-(4-cyano-phenyl)-thiazol-2-yl]-2-(2,4-difluoro-phenyl)-2-hydroxybutyl]-4-(3,5-dimethyl-4-methylaminoacetoxy-benzyl)-1H-[1,2,4]triazol-4-ium chloride hydrochloric acid salt, and 1-[2R,3R)-3-[4-(4-cyano-phenyl)-thiazol-2-yl]-2-(2,4-difluoro-phenyl)-2-hydroxybutyl]-4-(3,5-dimethyl-4-methylaminoacetoxy-benzyl)-1H-[1,2,4]triazol-4-ium bromide hydrobromic acid salt.

PROCESS A

The novel azole compounds represented by the general formula (I) as well as salts, hydrates or solvates thereof can be manufactured by reacting an azole compound possessing antifungal activity, of the general formula (II)

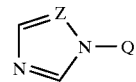

(II)

with a compound of the general formula (III),

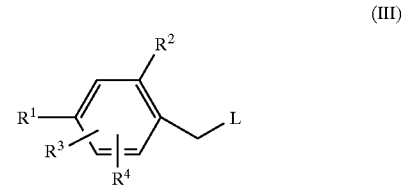

(III)

wherein $R^1$ and $R^2$ are each independently a hydrogen atom or a group —OY [in which Y is a group easily hydrolyzable under physiological conditions]; $R^3$ and $R^4$ are each independently a hydrogen or halogen atom, lower alkyl, lower alkoxy, lower alkylthio, (lower alkylcarbonyl) thiomethyl, carboxy or methoxycarbonyl; and L is a leaving group; or

PROCESS B

The novel azole compounds represented by the general formula (I) as well as salts, hydrates or solvates thereof can be manufactured by reacting a compound of the general formula (II) as defined above with a compound of the general formula (III) wherein one of $R^1$ or $R^2$ is hydroxy, followed by reaction of the resulting compound with a compound of formula $R^5COL$, or $(R^6O)2POL$, wherein $R^5CO$ is the acyl residue of a N-protected amino acid, or $R^5$ is hydrogen, lower alkoxy, lower alkyl which may be optionally substituted with carboxyl, amino, lower alkyl amino with or without protecting group, di-lower alkyl amino, or aryl; and $R^6$ is hydrogen or lower alkyl, and L is a leaving group such as chlorine, bromine, $OCOR^5$, methanesulfonyl, p-toluenesulfonyl and the like.

The reactions of processes A and B, of the compound of the general formula (II) with the compound of the general formula (III) can be carried out in a solvent such as methylene chloride, chloroform, benzene, toluene, acetonitrile, tetrahydrofuran, dioxane, or dimethylformamide, preferably chloroform, acetonitrile, or dimethylformamide.

The reaction time in the above benzylation reaction may be varied within a relatively wide range. In general, the reaction can be carried out at a temperature between 0° C. and 100° C., preferably between 0° C. and 50° C.

In process B, the acylation or phosphorylation can be performed with either free acid in the presence of a condensation agent such as 1-(3-dimethylaminopropyl)-3-ethylcarbodiimide hydrochloride and the like, or acid halides, acid anhydrides, mixed anhydrides, alkoxycarbonyl halides, dialkoxy phosphoryl chloride or phosphoryl chloride in the presence of an acid acceptor such as triethylamine, pyridine, picoline, lutidine, dimethylaminopyridine or alkali metal carbonate by the method known to those skilled in the art.

Preferably, an amino group present in $R^5$ in the compound of formula III is protected by a suitable amino protecting group as tert.-butoxy carbonyl.

The protecting group may, if necessary, be removed after the reaction by procedures known to those skilled in the art.

The compounds of formula I may contain an amino acid ester substituent $R^1$ and/or $R^2$ which substituents may form acid addition salts. The term "salts of compounds of formula I" refers to such acid addition salts. These salts may be derived from pharmaceutically acceptable acids as described earlier with reference to the Symbol $X^-$. The salt formation can be performed when removing a protecting group, or can be performed ad hoc by procedures known per se.

The hydration can be effected in the course of the manufacturing process or can occur gradually as a result of hygroscopic properties of an initially anhydrous product. Solvates with pharmaceutically acceptable solvents such as ethanol can be obtained for example, during crystallization.

The novel azole compounds represented by the general formula (I) as well as hydrates or solvates thereof have much higher water solubility than known antimycotic azole compounds he general formula (II) (see table 1).

TABLE 1

| Compound (Example No.) | solubility (mg/ml) | solvent* |
|---|---|---|
| 1 | 1.0 | b |
| 2 | 0.4 | b |
| 3 | 0.4 | b |
| 4 | >2.0 | a |
| 5 | >1.0 | a |
| 6 | 6.5 | a |
| 7 | >1.0 | a |
| 8 | 14.0 | a |
| 9 | >2.0 | a |
| 10 | >2.0 | a |
| 11 | 6.0 | a |
| 12 | 5.0 | a |
| 13 | 0.5 | b |
| 31 | 80 | a |

*solvent a = distilled water, solvent b = Mellvaine buffer(pH8.02)

In addition, the novel azole compounds are chemically stable in aqueous solution at room temperature more than three days, but are efficiently converted into compounds of formula (II) in either mouse, rat, monkey or human plasma.

The conversion of representatives of the new azole compounds of the general formula (I) to ketoconazole and itraconazole, respectively, in human plasma are shown in table 2. The compounds of formula I were incubated with human plasma at a concentration of 10 μg/ml at 37° C. for up to 120 min.

TABLE 2

Conversion of the new new azole compounds to ketoconazole (KCZ) and itraconazole (ICZ) in human plasma

| Example No. | Conversion half-life (min) | Incubation time (min) | Observed (%) | |
|---|---|---|---|---|
| | | | Comp. I | KCZ |
| 9 | <1 | 5 | <5 | 89 |
| 11 | <1 | 5 | <5 | 100 |
| 4 | 8.4 | 20 | 19 | 74 |

TABLE 2-continued

Conversion of the new new azole compounds to ketoconazole (KCZ) and itraconazole (ICZ) in human plasma

| Example No. | Conversion half-life (min) | Incubation time (min) | Observed (%) | |
|---|---|---|---|---|
| 10 | 3.5 | 10 | <5 | 80 ICZ |
| 1 | 53 | 60 | 47 | 28 |

In vivo efficacy of the compounds of the present invention is shown in Table 3. Male Fisher rats, strain F344/DuCrj, were employed for experimental infection models such as systemic candidiasis, systemic aspergillosis and pulmonary aspergillosis model. Immunocompetent 4 weeks old rats were used for systemic candidiasis or systemic aspergillosis which occurred after infection with *Candida albicans* conidia of $5 \times 10^6$/rat or with *Aspergillus fumigatus* conidia of $6 \times 10^5$/rat via tail vein. Otherwise for pulmonary aspergillosis model, rats had been immunosuppressed with cortisone acetate treatments prior to infection with $2 \times 10^5$/rat intratrachially. Treatments were given twice on the first day and once daily on following 4 days both for systemic and pulmonary aspergillosis. For systemic candidiasis rats were treated at 0, 4, 24, and 48 h after infection. Effective dose 50% (ED50) values were determined on day 14 after infection.

TABLE 3

(μmol/kg)

| | Systemic candidiasis | | Pulmonay aspergillosis | | Systemic aspergillosis | |
|---|---|---|---|---|---|---|
| | i.v. | p.o. | i.v. | p.o. | i.v. | p.o. |
| Example 16 | 3.5 | <2.1 | 17 | 18 | >35 | >55 |
| Example 23 | 4.6 | 4.7 | 8.0 | 17 | 17 | 19 |
| Itraconazole | n.t. | n.t. | n.t. | n.t. | n.t. | 17 |
| Fluconazole | n.t. | >2.9 | n.t. | n.t. | n.t. | n.t. |

Therefore, the water soluble azole antifungal agents, represented by the general formula (I) as well as salts, hydrates or solvates thereof, according to the present invention, exhibit potent antifungal activity against various fungal infections including Aspergillosis in mice over a very wide range of dosages both orally and parenterally and are useful as antifungal agents.

The present invention further relates to the pharmaceutical compositions containing the azole compound of the general formula () as well as salts, hydrates or solvates thereof.

The azole compounds of the formula (I) as well as salts, hydrates or solvates thereof are very active antimycotic agents. They are active against a variety of fungal species including Candida spp., *Cryptotoccus neoformanis*, Aspergillus spp., Trichophyton spp., Microsporum spp., Exophiala spp., *Blastomyces dermatitidis,* and *Histoplasma capsulatum.*

Thus, the compounds of the present invention are useful for topical and systemic treatment of mycoses in animals as well as in humans. For example, they are useful in treating topical and mucosal fungal infections caused by, among other genera, Candida, Trichophyton, or Microsporum. They may also be used in the treatment of systemic fungal infections caused by, for example, Candida spp., *Cryptococcus neoformans,* Aspergillus spp., Paracoccidiodes spp., Sporotrix spp., Exophiala spp., Blastomyces spp., or Histoplasma spp.

For clinical use, the azole compound of the formula (I) as well as salts, hydrates or solvates thereof can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration.

Pharmaceutical formulation for oral administration may be granule, tablet, sugar coated tablet, capsule, pill, suspension or emulsion. For parenteral injection, for example, intravenously, intramuscularly or subcutaneously, the azoles of formula (I) may be used in the form of a sterile aqueous solution which may contain other substances, for example, salts or glucose to make the solution isotonic. The azoles can also be administered in the form of a suppository or pessary, or they may be applied topically in the form of a lotion, solution, cream, ointment or dusting powder.

The daily dosage level of the azole compounds of the formula (I) is from about 0.1 to about 50 mg/kg (in divided doses) when administered in one, two or more dosages by either the oral or parenteral route. Thus tablets or capsules of the compounds may contain from about 5 mg to about 0.5 g of active compound for administration. In any event the actual dosage can be determined by the physician and it may be varied upon the age, weight and response of the particular patient.

In addition, the azole compounds of the formula (I) as well as salts, hydrates or solvates thereof have activity against a variety of plant pathogenic fungi, including for example *Pyricularia oryzae, Pythium aphanidermatum,* Alternaria spp., and *Paecilomyces variotii.*

Thus, they can be applied for agricultural and horticultural purposes preferably in the form of a composition formulated as appropriate to the particular use and purpose desired, for example dusting powders, or granules, seed dressings, aqueous solutions, dispersions or emulsions, dips, sprays or aerosols. Such compositions may contain such conventional carriers, diluents or adjuvants as are known and acceptable in agriculture and horticulture. Other compounds having herbicidal or insecticidal, or additional antifungals can be incorporated in the compositions. The compounds and compositions can be applied in a number of ways, for example they can be applied directly to the plant foliage, stems, branches, seeds or roots or to the soil or other growing medium, and they may be used not only to eradicate the disease, but also prophylactically to protect the plants or seeds from attack.

EXAMPLES

The following examples merely illustrate the preferred methods for the preparation of the compounds of the present invention and are not intended to limit the scope of the invention thereto.

Example 1

Preparation of 4-(4-Acetoxy-3,5-dimethylbenzyl)-1-[4-(4-{4-[4-(1-(2-butyl)-5-oxo-1,5-dihydro-[1,2,4]triazol-4-yl)phenyl]piperazin-1-yl}phenoxymethyl)-2-(2,4-dichlorophenyl)-[1 3]dioxolan-2-ylmethyl]-1H-[1,2,4]triazol-4-ium bromide To a solution of 1 g of 3,5-dimethyl-4-hydroxybenzyl bromide in CHCl$_3$—CH$_3$CN (7/3 ml) was added 400 mg of Itraconazole and stirring was continued for 15 h at room temperature. The solvent was evaporated in vacuo and the residue was stirred in acetic anhydride-pyridine (4/4 ml) for 2 h at ambient temperature. The mixture was concentrated and column chromatography on silica gel (200 Å, solvent: CH$_2$Cl$_2$/MeOH=10/1) gave 4-(4-acetoxy-3,5-dimethylbenzyl)-1-[4-(4-{4-[4-(1-(2-butyl)-5-oxo-1,5-dihydro-[1,2,4]triazol-4-yl)phenyl]piperazin-1-yl}phenoxymethyl)-2-(2,4-dichlorophenyl)-[1,3]dioxolan-2-ylmethyl]-1H-[1,2,4]triazol-4-iumbromide (507 mg, 93%, as amorphous powder);

FAB-MS: m/z 881 (M-Br)+; 1H-NMR(CDCl3) δ0.90 (3H,t,J=7.3 Hz), 1.39(3H,d,J=6.9 Hz), 1.69~1.77(1H,m), 1.81~1.87(1H,m), 2.02(3H,s), 2.10(3H,s), 2.32(3H,s), 3.22~3.29(2H,m), 3.31~3.38(1H,m), 3.66~3.74 (1H,m), 3.85~3.91(1H,m), 4.11~4.15(1H,m), 4.28~4.33(2H,m), 4.35~4.45(1H,m), 5.02(1H,d,J=14.2 Hz), 5.03(1H,d,J=14.5 Hz), 5.13(1H,d,J=14.5 Hz), 5.54(1H,d,J=14.2 Hz), 6.88~7.04(8H,m), 7.29(1H,dd,J=2.0,7.3 Hz), 7.45(1H,d,J= 8.9), 7.47(1H,d,J=2.0), 7.62(1H,s), 7.68(1H,d, J=8.2), 8.02 (1H,s), 11.5~11.6(1H,brs).

The following compounds in Examples 2~8 were obtained according to a manner analogous to that of Example 1.

Example 2

4-(4-(Pyridine-3-carbonyloxy)-3,5-dimethylbenzyl)-1-[4-(4-{4-[4-(1-(2-butyl)-5-oxo-1,5-dihydro-[1,2,4]triazol-4-yl)phenyl]piperazin-1-yl}phenoxymethyl)-2-(2,4-dichlorophenyl)-[1,3]dioxolan-2-ylmethyl]-1H-[1,2,4]triazol-4-ium bromide Physical form: amorphous powder; MALDI-TOF-MS: m/z 945 (M—Br)+; 1H-NMR(CD3OD) δ0.88(3H,t,J=7.6 Hz), 1.36(3H,d,J=5.3 Hz), 1.73(2H,m), 2.16(6H,s), 3.30(8H, m), 3.63~4.44(6H,m), 5.18(2H,s), 5.48(2H,s), 6.84~8.56 (18H,m), 9.01(1H,s).

Example 3

4-(4-Benzoyloxy-3,5-dimethylbenzyl)-1-[4-(4-{4-[4-(1-(2-butyl)-5-oxo-1,5-dihydro-[1,2,4]triazol-4-yl)phenyl]piperazin-1-yl}phenoxym ethyl)-2-(2,4-dichlorophenyl)-[1,3dioxolan-2-ylmethyl]-1H-[1,2,4]triazol-4-ium bromide Physical form: amorphous powder; FAB-MS: m/z 943 (M—Br)+; 1H-NMR(d6-DMSO) δ0.80(3H,t,J=7.3 Hz), 1.29(3H,d,J=6.6 Hz), 1.67(2H, m), 2.11(6H,s), 3.40(8H, brs), 3.77(2H,m), 3.95(2H,m), 4.12(1H,m), 4.40(1H,m), 5.08(2H,s), 5.42(2H,s), 6.90(2H,brd), 7.11~7.80(14H,m), 8.17(2H,d,J=7.2 Hz), 8.35(1H,s), 9.40(1H,s), 10.4(1H,s).

Example 4

1-(4-Acetoxy-3,5-dimethyl-benzyl)-3-[(2R*,4S*)-4-[4-(4-acetyl-pipera zin-1-yl)-phenoxymethyl]-2-(2,4-dichloro-phenyl)-[1,3]dioxolan-2-ylmethyl]-3H-imidazol-1-ium bromide Physical form: pale brown oil; FAB-MS: m/z 707 (M—Br)+; 1H-NMR(CDCl3) δ2.11(6H,s), 2.14(3H,s), 2.33 (3H,s), 3.07(4H,m), 3.62(2H,m), 3.68(1H, dd,J=4.6,10.2 Hz), 3.77(2H,m), 3.89~3.95(2H,m), 4.02(1H,dd,J=4.0,11.6 Hz), 4.37(1H,m), 4.85(2H,s), 5.08(1H,d,J=14.2 Hz), 5.48 (1H,d,J=14.2 Hz), 6.81(2H,d,J=8.9 Hz), 6.91(2H,d,J=8.9 Hz), 6.99(1H,s), 7.05(2H,s), 7.18(1H,s), 7.31(1H,dd,J=2.0, 8.6 Hz), 7.47(1H,d,J=2.0 Hz), 7.69(1H,d,J=8.6 Hz), 10.42 (1H,s).

Example 5

3-1(2R*,4S*)-4-[4-(4-Acetyl-piperazin-1-yl)-phenoxymethyl1-2-(2,4-dichloro-phenyl)-[1,3]dioxolan-2-ylmethyl]-1-(4-isobutyryloxy-3,5-dimethyl-benzyl)-3H-imidazol-1-ium bromide Physical form: clear film; FAB-MS: m/z 735 (M—Br)+; 1H-NMR(CDCl3) δ 1.34(6H,d,J=6.9 Hz), 2.09(6H,s), 2.14 (3H,s), 2.85(1H, sept,J=6.9 Hz), 3.06(4H,m), 3.61 (1H,dd, J=4.9,5.2 Hz), 3.67(1H,dd,J=4.0, 10.6 Hz), 3.97(1H,dd,J= 4.9,5.2 Hz), 3.90(2H,m), 3.97(1H,dd,J=4.0,10.6 Hz), 4.35 (1H,m), 4.83(2H,s), 5.15(1H,d,J=14.5 Hz), 5.49(1H,d,J= 14.5 Hz), 6.80(2H,d,J=8.9 Hz), 6.91(2H,d,J=8.9 Hz), 7.08 (2H,s), 7.10(1H,d,J=2.0 Hz), 7.19(1 H,brs), 7.30(1 H,dd,J= 2.0,8.3 Hz), 7.46(1 H,d,J=2.0 Hz), 7.67(1H,d,J=8.3 Hz), 10.32(1H,brs).

Example 6

1-(4-Acetoxy-3,5-dichloro-benzyl)-3-[(2R*,4S*)-[4-F4-(4-acetyl-piperazin-1-yl)-phenoxymethyl]-2-(2,4-dichloro-phenyl)-[1,3]dioxolan-2-ylmethyl]-3H-imidazol-1-ium bromide Physical form pale brown oil; FAB-MS: m/z 747 (M—Br)+; 1H-NMR(CDCl3) δ2.14(3H,s), 2.39(3H,s), 3.07 (4H,m), 3.62(3H,m), 3.78(2H,m), 3.89(1H,m), 3.97(1H,m), 4.10(1H,m), 4.39(1H,m), 4.75 (1H,d,J=16.2 Hz), 4.83(1H, d,J=16.2 Hz), 5.11(1H,d,J=14.8 Hz), 5.77(1H,d,J=14.8 Hz), 6.79(2H,d,J=9.1 Hz), 6.92(2H,d,J=9.1 Hz), 7.01(1H,s), 7.22 (1H,s), 7.33(1H,dd,J=8.6,2.0 Hz), 7.42(2H,s), 7.48(1H,d,J= 2.0 Hz), 7.68(1H,d,J=8.6 Hz), 10.52(1H,s).

Example 7 dl-1-(4-Acetoxy-3,5-dimethyl-benzyl)-3-[2-(2,4-dichloro-benzyloxy)-2-(2,4-dichloro-phenyl)-ethyl]-3H-imidazol-1-ium bromide Physical form: amorphous powder; FAB-MS: m/z 593 (M—Br)+; 1H-NMR(CD3OD) δ2.15(6H,s), 2.35(3H,s), 4.41~4.58(4H,m), 5.22(1H,dd,J=3.5,7.8 Hz), 5.32(2H,s), 7.16(2H,brs), 7.24~7.56(7H,m), 7.66(1H,d,J=1.0 Hz), 9.00 (1H, brs).

Example 8

4-(4-acetoxy-3,5-dimethyl-benzyl)-1-[(1R,2S,6R)-2-methoxy-3,3-dimethyl-6-(2-p-tolyl-ethyl)-cyclohexylmethyl]-1H-[1,2,4]triazol-4-ium bromide Physical form: colorless oil; MALDI-TOF-MS: m/z 518 (M—Br)+; 1H-NMR(CDCl3) δ0.84(3H,s), 1.02(3H,s), 1.10~1.30(3H,m), 1.37~1.42 (1H,m), 1.45~1.65(1H,m), 1.71(1H,m), 1.93(2H,m), 2.15(6H,s), 2.31 (3H,s), 2.34(3H, s), 2.51(1H,m), 2.71(1H,m), 2.83(1H,d,J=10.9 Hz), 3.50 (3H,s), 4.49(1H,d,J=18.9 Hz), 4.60(1H,dd,J=18.9,5.9 Hz), 5.58(1H,d,J=14.4 Hz), 5.66(1H,d,J=14.4 Hz), 7.08(4H,s), 7.21(2H,s), 8.31(1H,s), 11.64(1H,s).

Example 9

Preparation of 1-(4-Acetoxybenzyl)-3-[(2R*,4S*)-4-[4-(4-acetylpiper azin-1-yl)phenoxymethyl]-2-(2,4-dichlorophenyl)-[1,3]dioxolan-2-yl methyl]-3H-imidazol-1-ium bromide To a solution of 28 mg of 4-acetoxybenzyl bromide in 1.5 mL of CHCl3 was added 30 mg of Ketoconazole and the mixture was stirred for 16 h at room temperature. The solvent was evaporated in vacuo. Column chromatography on silica gel(Wakogel C-200, solvent:CH2Cl2/MeOH=10/1) gave 1-(4-acetoxybenzyl)-3-[(2R*,4S*)-4-[4-(4-acetyl piperazin-1-yl)phenoxymethyl]-2-(2,4-dichlorophenyl)-[1,3]dioxolan-2-yl methyl]-3H-imidazol-1-ium bromide (32 mg, 76%, as colorless oil); MALDI-TOF-MS m/z 679 (M—Br)+; 1H-NMR(CDCl3) δ2.14(3H,s), 2.28(3H,s), 3.05 (4H,m), 3.60~3.89(8H,m), 4.33(1H,m), 4.80(2H,s), 5.37 (1H,d,J=14.5 Hz), 5.61(1H,d,J=14.5 Hz), 6.78(2H,d,J=9.1 Hz), 6.92, (2H,d,J=9.1 Hz), 7.03(2H,d,J=8.6 Hz), 7.24~7.63 (7H,m), 10.1(1H,s).

The following compounds in Example 10~13 were obtained according to a manner analogous to that of Example 9.

Example 10

3-[(2R*,4S*)-4-[4-(4-Acetylpiperazin-1-yl)phenoxymethyl]-2-(2,4-dichlorophenyl)-[1,3]dioxolan-2-ylmethyl]-1-[4-(2,2-dimethylpropionyloxy)benzyl]-3H-imidazol-1-ium bromide Physical form: amorphous powder; MALDI-TOF-MS: m/z 721 (M—Br)+; 1H-NMR (CDCl3) δ1.34(9H,s), 2.14 (3H,s), 3.06(4H,m), 3.60~4.00(8H,m),4.36, (1H,m), 4.81 (2H,s), 5.29(1H,d,J=14.4 Hz), 5.62(1H,d,J=1 4.4 Hz), 6.80 (2H,d,J=9.3 Hz), 6.92(2H,d,J=9.3 Hz), 7.02(2H,d,J=8.6 Hz), 7.15(1H,brs), 7.20(1H,brs), 7.28(1H,brs), 7.43(2H,d,J=8.6 Hz), 7.46(1H,brs), 7.65(1H,d,J=8.3 Hz), 10.3(1H,s).

Example 11

1-(4-Acetoxy-3-methyl-benzyl)-3-[(2R*,4S*)-4-[4-(4-acetyl-piperazin-1-yl)-phenoxymethyl]-2-(2,4-dichloro-phenyl)-[1,3]dioxolan-2-ylmethyl]-3H-imidazol-1-ium bromide Physical form: clear film; FAB-MS: m/z 693(M—Br)+; 1H-NMR(CDCl3) δ2.13(6H,s), 2.31(3H,s), 3.06(4H,dt,J= 5.0 Hz), 3.62(2H,t,J=5.0 Hz), 3.66(1H,dd,J=4.6 Hz), 3.76 (2H,t,J=9.0 Hz), 3.88(2H,m), 3.94(1H,dd,J=4.6 Hz), 4.36 (1H,m), 4.81(2H,s), 5.26(1H,d,J=14.0 Hz), 5.55(1H,d,J= 14.0 Hz), 6.79(2H,d,J=9.0 Hz), 6.91(2H,d,J=9.0 Hz), 6.96 (1H,d,J=8.0 Hz), 7.22(2H,brs), 7.23(1H,dd,J=2.0,8.0 Hz), 7.29(1H,dd,J=2.0,8.0 Hz), 7.39(1H,brd), 7.45(1H,d,J=2.0 Hz), 7.64(1H,d,J=8.0 Hz), 10.21(1H,s).

Example 12

1-(4-Acetoxy-3-methoxyl-benzyl)-3-[(2R*,4S*)-4-[4-(4-acetyl-piperazin-1-yl)-phenoxymethyl]-2-(2,4-dichloro-phenyl)-[1,3]dioxolan-2-yl methyl]-3H-imidazol-1-ium bromide Physical form: amorphous powder; MALDI-TOF-MS: m/z 709(M—Br)+; 1H-NMR(CDCl3) δ2.14(3H,s), 2.30 (3H,s), 3.06(4H,m), 3.62(2H,m), 3.65(1H,dd,J=4.6,10.2 Hz), 3.77(2H,m), 3.86(3H,s), 3.88~3.94(2H,m), 4.03(1H, dd,J=4.0,11.6 Hz), 4.36(1H,m), 4.80(2H,s), 5.12(1H,d,J= 14.2 Hz), 5.54(1H,d,J=14.2 Hz), 6.80(2H,d,J=8.9 Hz), 6.81 (1H,s), 6.92 (2H,d,J=8.9 Hz), 6.95(1H,s), 7.07(1H,s), 7.17 (1H,s), 7.31(1H,dd,J=2.0,8.6 Hz), 7.44(1H,d,J=2.0 Hz), 7.47(1H,J=2.0 Hz), 7.66(1H,d,J=8.6 Hz), 10.41(1H,s).

Example 13 dl-1-[4-(4-{4-[4-(1-sec-butyl-5-oxo-1 5-dihydro-[1,2,4]triazol-4-yl)-phenyl]-piperazin-1-yl}-phenoxymethyl)-2-(2,4-dichloro-phenyl)-[1,3]dioxolan-2-ylmethyl]-4-(4-hexanoyloxy-3,5-dimethyl-benzyl)-1H-[1,2,4]triazol-4-ium methanesulfonate Physical form: amorphous powder; FAB-MS: m/z 937 (M-MsO)+; 1H-NMR(CDCl3) δ0.80~1.00(6H,m), 1.42(3H, d,J=6.6 Hz), 1.20~1.50 (6H,m), 1.70~2.00(2H,m), 2.10(9H, s), 2.58(2H,t,J=7.6 Hz), 3.26(4H,m), 3.36(4H,m),3.62~3.70 (2H,m), 3.75(1H,m), 4.10~4.50(3H,m), 4.84(1H,d,J=14.2 Hz), 5.00(1H,d,J=13.8 Hz), 5.12(1H,d,J=13.8 Hz), 5.44(1H, d,J=14.2 Hz), 6.90(2H,d,J=8.9 Hz), 6.94(2H,s), 6.99(2H,d, J=8.9 Hz), 7.03(2H,d,J=8.9 Hz), 7.31(1H,dd,J=8.6,2.0 Hz), 7.43(2H,d,J=8.9 Hz), 7.48(1H,d,J=2.0 Hz), 7.62(1H,s), 7.71 (1H,d,J=8.6 Hz), 7.90(1H,s), 11.30(1H,s).

Example 14

(2R,3R)-4-(4-Acetyloxy-3,5-dimethylbenzyl)-1-[3-[4-(4-cyanophenyl)-thiazol-2-yl]-2-(2,4-difluorophenyl)-2-hydroxy-butyl]-1H-[1,2,4]triazol-4-ium bromide Physical form amorphous poweder; FAB-MS: m/z 614 (M—Br)+; $^1$H-NMR(CD$_3$OD) δ1.24(3H,d,J=6.9 Hz), 2.25 (6H,s), 2.36(3H,s), 4.30(1H,q,J=6.9 Hz), 4.64(1H,d,J=14.2 Hz), 5.10(1H,d,J=14.2 Hz), 5.31(2H,s), 6.75–7.27(3H,m), 7.10(2H,s), 7.82(2H,d,J=8.3 Hz), 8.09(1H,s), 8.18(2H,d,J= 8.2 Hz), 8.73(1H,s), 9.95(1H,s).

Example 15

(2R,3R)-4-(4-Aminoacetoxy-2-carboxy-benzyl)-1-F3-[4-(4-cyano-phenyl)-thiazol-2-yl]-2-(2,4-difluorophenyl)-2-hydroxybutyl]-1H-[1,2,4]triazol-4-ium bromide trifluoroacetic acid salt a) Preparation of 3-(tert-butoxycarbonylaminoacetoxy)-6-(bromomethyl)benzoic acid tert-butyl ester A mixture of 200 mg of 3-hydroxy-6-(hydroxymethyl) benzoic acid tert-butyl ester, 187 mg of Boc-glycine, 65 mg of 4-dimethylaminopyridine and 245 mg of I-(3-dimethylaminopropyl)-3-ethylcarbodiimide hydrochloride in 8 mL of dichloromethane was stirred for 15 h at room temperature and was diluted with 40 mL of dichloromethane. The mixture was washed with 1N HCl and dried over anhydrous Na$_2$SO$_4$.

Removal of the solvent gave 180 mg of 3-(tert-butoxycarbonylaminoacetoxy)-6-hydroxymethylbenzoic acid tert-butyl ester.

To a solution of 650 mg of 3-(tert-butoxycarbonylaminoacetoxy)-6-hydroxymethylbenzoic acid tert-butyl ester and 580 mg of triphenylphosphine was added 848 mg of carbon tetrabromide, and the mixture was stirred for 2 h at room temperature. The mixture was diluted with dichloromethane and washed with water. The organic layer was dried over anhydrous Na$_2$SO$_4$ and concentrated in vacuo. Column chromatography on silica gel gave 322 mg of 3-(tert-butoxycarbonylaminoacetoxy)-6-(bromomethyl) benzoic acid tert-butyl ester as a colourless oil; $^1$H-NMR (CDCl$_3$) δ1.34(9H,s), 1.51 (9H,s), 4.08(2H,br.d,J=5.6 Hz), 4.80(2H,s), 4.95(1H,br.s), 7.12(1H,dd,J=8.6,2.6 Hz), 7.34 (1H,d,J=8.6 Hz), 7.51(1H,d,J=2.6 Hz)

b) (2R,3R)-4-(4-Aminoacetoxy-2-carboxybenzyl)-1-[3-[4-(4-cyanophenyl)thiazol-2-yl]-2-(2,4-difluorophenyl)-2-hydroxybutyl]-1H-[1,2,4]triazol-4-ium bromide trifluoroacetic acid salt was obtained as a white solid from (1R,2R)-4-[2-[2-(2,4-difluoro-phenyl)-2-hydroxy-1-methyl-3-[1,2,4] triazol-1-yl-propyl]-thiazol-4-yl]-benzonitrile and 3-(tert-butoxycarbonylaminoacetoxy)-6-(bromomethyl)benzoic acid tert-butyl ester according to a manner analogous to that of Example 1;

Physical form: white powder; FAB-MS: m/z 645 (M—Br)+; $^1$H-NMR(CD$_3$OD) δ1.22(3H,d,J=7.3 Hz), 4.21 (2H,s), 4.28(1H,q,J=7.3 Hz), 4.61(1H,d,J=14.2 Hz), 5.09 (1H,d,J=14.2 Hz), 5.68(1H,d,J=14.0 Hz), 5.75(1H,d,J=14.0 Hz), 6.78–7.28(3H,m), 7.55(1H,dd,J=2.3,8.6 Hz), 7.64(1H, d,J=8.6 Hz), 7.81(2H,d,J=8.5 Hz), 8.03(1H,d,J=2.3 Hz), 8.10(1H,s), 8.17(2H,d,J=8.5 Hz), 8.67(1H,s), 9.80(1H,s).

Example 16

1-[(2R,3R)-3-[4-(4-Cyanophenyl)-thiazol-2-yl]-2-(2,4-difluorophenyl)-2-hydroxybutyl]-4-[(S)-3,5-dimethyl-4-(pyrrolidine-2-carbonyloxy)-benzyl]-1H-[1,2,4]triazol-4-ium bromide trifluoroacetic acid salt was obtained either by the following method A or B.

i) method A:

To a solution of 3 g of 3,5-dimethyl-4-hydroxybenzyl bromide in CH$_3$CN(30 mL) was added 1.2 g of (1R,2R)-4-[2-[2-(2,4-difluorophenyl)-2-hydroxy-1-methyl-3-[1,2,4] triazol-1-yl-propyl]thiazol-4-yl]benzonitrile and stirring was continued for 2 h at room temperature. The precipitate was filtered and washed with ether to give 1.37 g(81 %y.) of 1-[(2R,3R)-3-[4-(4-cyanophenyl)thiazol-2-yl]-2-(2,4-difluorophenyl)-2-hydroxybutyl]-4-(3,5-dimethyl-4-hydroxy)benzyl-1H-[1,2,4]triazol-4-ium bromide(RoO9-3846) as a white solid. To a mixture of 30 g of 1-[(2R,3R)-3-[4-(4-cyanophenyl)thiazol-2-yl]-2-(2,4-difluoro-phenyl)-2-hydroxybutyl]-4-(3,5-dimethyl-4-hydroxybenzyl)-1H-[1, 2,4]triazol-4-ium bromide, 10.9 g of Boc-(L)-proline and 2.8 g of N,N-dimethylaminopyridine in 1.2L of dichloromethane was added 17.6 g of 1-(3-dimethylaminopropyl)-3-ethylcarbodiimide hydrochloride and the mixture was stirred for 1.5 h at room temperature and concentrated in vacuo. The residue was chromatographed on silica gel (Wakogel C-200, solvent: CH$_2$Cl$_2$/MeOH=14/1) to give 30.9 g(79%y.) of 1-[(2R,3R)-3-[4-(4-cyanophenyl)thiazol-2-yl]-2-(2,4-difluorophenyl)-2-hydroxybutyl]-4-[(S)-3,5-dimethyl-4-(N-tert-butoxycarbonylpyrrolidine-2-carbonyloxy)benzyl]-1H-[1,2,4]triazol-4-ium bromide as a white solid. 30.9 g of 1-[(2R,3R)-3-[4-(4-cyanophenyl) thiazol-2-yl]-2-(2,4-difluorophenyl)-2-hydroxybutyl]-4-[(S)-3,5-dimethyl-4-(N-tert-butoxycarbonylpyrrolidine-2-carbonyloxy)benzyl]-1H-[1,2,4]triazol-4-ium bromide was stirred in 600 mL of 10% TFA-dichloromethane for 5 h at room temperature and the solvent was removed in vacuo. The residue was diluted with ether and the precipitate was washed with ether to give 1-[(2R,3R)-3-[4-(4-cyanophenyl) thiazol-2-yl]-2-(2,4-difluorophenyl)-2-hydroxybutyl]-4-[(S)-3,5-dimethyl-4-(pyrrolidine-2-carbonyloxy)benzyl]-1H-[1,2,4]triazol-4-ium bromide trifluoroacetic acid salt as a white solid.

ii) method B:

A mixture of 1.06 g of (1R,2R)-4-[2-[2-(2,4-difluorophenyl)-2-hydroxy-1-methyl-3-[1,2,4]triazol-1-yl-propyl]thiazol-4-yl]benzonitrile and 1.1 g of 3,5-dimethyl-4-[(S)-N-tert-butoxycarbonylpyrrolidine-2-carbonyloxy] benzyl bromide, prepared from 3,5-dimethyl-4-hydroxybenzaldehyde in 3 steps, in 20 mL of acetonitrile was stirred for 15 h at reflux temperature and then concentrated. The residue was chromatographed on silica gel (Wakogel C-200, solvent: CH$_2$Cl$_2$/MeOH=12/1) to give 1.92 g (94%y.) of 1-[(2R,3R)-3-[4-(4-cyanophenyl)thiazol-2-yl]-2-(2,4-difluorophenyl)-2-hydroxybutyl]-4-[(S)-3,5-dimethyl-4-(N-tert-butoxycarbonylpyrrolidine-2-carbonyloxy)benzyl]-1H-[1,2,4]triazol-4-ium bromide as a white solid.

1-[(2R,3R)-3-[4-(4-Cyanophenyl)thiazol-2-yl]-2-(2,4-difluorophenyl)-2-hydroxybutyl]-4-[(S)-3,5-dimethyl-4-(pyrrolidine-2-carbonyloxy)benzyl]-1H-[1,2,4]triazol-4-ium bromide trifluoroacetic acid salt was obtained by removal of the protecting group as described in the method A;

Physical form: white powder; MALDI-TOF-MS: m/z 669 (M—Br)+; $^1$H-NMR(CD3OD) δ1.24(3H,d,J=7.3 Hz), 2.18–2.25(2H,m), 2.21(6H,s), 2.36–2.44(1H,m), 2.66–2.71 (1H,m), 3.43–3.50(2H,m), 4.30(1H,q,J=7.3 Hz), 4.65(1H,d, J=14.2 Hz), 4.88(1H,m), 5.12(1H,d,J=14.2 Hz), 5.33(2H,s), 6.73–6.79(1H,m), 6.99–7.06(1H,m), 7.14(2H,s), 7.21–7.30 (1H,m), 7.82(2H,d,J=8.6 Hz), 8.10(1H,s), 8.18(2H,d,J=8.6 Hz), 8.74(1H,s), 10.00(1H,s)

Following compounds in Example 17–30 were obtained according to a manner analogous to that of Example 16.

Example 17

(2R,3R)-4-(4-Aminoacetoxy-3,5-dimethylbenzyl)-1-[3-[4-(4-cyanophenyl)-thiazol-2-yl]-2-(2,4-difluorophenyl)-2-hydroxybutyl]-1H-[1,2,4]triazol-4-ium bromide trifluoroacetic acid salt Physical form: white powder; FAB-MS: m/z 629 (M—Br)+; $^1$H-NMR(CD3OD) δ1.25(3H,d,J=7.3 Hz), 2.21 (6H,s), 4.29(1H,q,J=7.3 Hz), 4.31(2H,s), 4.66(1H,d,J=14.2 Hz), 5.12(1H,d,J=14.2 Hz), 5.34(2H,s), 6.72–7.30(3H,m), 7.15(2H,s), 7.81(2H,d,J=6.6 Hz), 8.10(1H,s), 8.17(2H,d,J=6.6 Hz), 8.74(1H,s), 10.0(1H,s).

Example 18

(2R,3R)-4-[4-(3-Aminopropionyloxy)-3,5-dimethylbenzyl]-1-[4-F4-(4-cyanophenyl)-thiazol-2-yl]-2-(2,4-difluorophenyl)-2-hydroxy-3-methylbutyl]-1H-[1,2,4]triazol-4-ium bromide trifluoroacetic acid salt Physical form: white powder; FAB-MS: m/z 643 (M-TFA—Br)+; $^1$H-NMR(CD3OD) δ1.24(3H, t, J=7.3 Hz), 2.19(6H, s), 3.09~3.37(4H, m), 4.30(1H, q, J=7.3 Hz), 4.66(1H, d, J=14.2 Hz), 5.11 (1H, d, J=14.2 Hz), 5.33(2H, br. s), 6.73~6.81(1H, m), 6.98~7.07(1H, m), 7.12(2H, s), 7.20–7.33(1H, m), 7.81(2H, d, J=6.9 Hz), 8.10(1H, s), 8.18(2H, d, J=6.9 Hz), 8.74(1H, s), 10.00(1H, s).

Example 19

(2R,3R)-4-[4-(4-Aminobutyryloxy)-3,5-dimethylbenzyl]-1-[4-[4-(4-cyanophenyl)-thiazol-2-yl]-2-(2,4-difluorophenyl)-2-hydroxy-3-methylbutyl]-1H-[1,2,4]triazol-4-ium bromide trifluoroacetic acid salt Physical form: white powder; FAB-MS: m/z 657 (M-TFA—Br)+; $^1$H-NMR(CD3OD) δ 1.24(3H, d, J=7.26 Hz), 2.03~2.12(2H, m), 2.17(6H, s), 2.87(2H, t, J=7.5 Hz), 3.07(2H, t, J=7.5 Hz), 4.30(1H, t, J=7.5 Hz), 4.65(1H, d, J=14.4 Hz) 5.10(1H, d, J=14.4 Hz), 5.31(2H, s), 6.73~6.80 (1H, m), 6.98–7.07(1H, m), 7.11(2H, s), 7.18–7.28(1H, m), 7.82(2H, d, J=8.6 Hz), 8.10(1H, s), 8.17(2H, d, J=8.6 Hz), 8.73(1H,s).

Example 20

(2R,3R)-4-[4-[(2-Aminoacetylamino)acetoxyl-3,5-dimethylbenzyl]-1-[3-[4-(4-cyanophenyl)-thiazol-2-yl]-2-(2,4-difluorophenyl)-2-hydroxybutyl]-1H-[1,2,4]triazol-4-ium bromide trifluoroacetic acid salt Physical form: white powder; FAB-MS: m/z 686 (M—Br)+; $^1$H-NMR(DMSO-d6) δ1.18(3H,d,J=6.9 Hz), 2.08(6H,s), 3.67(2H,brs), 4.14(1H,q,J=6.9 Hz), 4.34(2H,d, J=5.6), 4.69(1H,d,J=14.2 Hz), 5.01(1H,d,J=14.2 Hz), 5.35 (2H,s), 6.58(1H,s), 6.90–6.96(1H,m), 7.07(2H,s), 7.21–7.37 (2H,m), 7.94(2H,d,J=7.9 Hz), 8.07(2H,brs), 8.21(2H,d,J= 7.9 Hz), 8.43(1H,s), 8.99(1H,t,J=5.6), 9.02(1H,s), 10.06(1H, s).

Example 21

1-[(2R,3R)-3-[4-(4-Cyanophenyl)-thiazol-2-yl]-2-(2, 4-difluorophenyl)-2-hydroxy-butyl]-4-[4-[(S)-2,5-diaminopentoyloxyl-3,5-dimethylbenzyl]-1H-[1,2,4] triazol-4-ium bromide trifluoroacetic acid salt Physical form: white powder; FAB-MS: m/z 686 (M—Br)+; $^1$H-NMR(CD3OD) δ1.24(3H,d,J=6.9 Hz), 1.95–2.43(4H,m), 2.22(6H,s), 3.09(2H,t,J=7.0 Hz), 4.30 (1H,q,J=6.9 Hz), 4.60(1H,m), 4.67(1H,d,J=14.2 Hz), 5.12 (1H,d,J=14.2 Hz), 5.34(2H,s), 6.76–7.27(3H,m), 7.15(2H, s), 7.82(2H,d,J=8.2 Hz), 8.10(1H,s), 8.18(2H,d,J=8.2 Hz), 8.74(1H,s), 10.0(1H,s).

Example 22

4-[4-[(S)-2-Aminopropionyloxy)-3,5-dimethylbenzyl]-1-[(2R,3R)-3-[4-(4-cyanophenyl)-thiazol-2-yl]-2-(2,4-difluorophenyl)-2-hydroxybutyl]-1H-[1,2,4]triazol-4-ium bromide trifluoroacetic acid salt Physical form: white powder; FAB-MS: m/z 643 (M—Br)+; $^1$H-NMR(CD3OD) δ1.23(3H,d,J=6.9 Hz), 1.79 (3H,d,J=6.9 Hz), 2.20(6H,s), 4.29 (1H,q,J=6.9 Hz), 4.57 (1H,q,J=6.9 Hz), 4.67(1H,d,J=14.2 Hz), 5.12(1H,d,J=14.2 Hz), 5.34(2H,s), 6.70–7.26(3H,m), 7.14(2H,s), 7.80(2H,d, J=8.2 Hz), 8.10(1H,s), 8.18(2H,d,J=8.2 Hz), 8.74(1H,s), 10.0(1H,s).

Example 23

1-[(2R,3R)-3-[4-(4-Cyanophenyl)thiazol-2-yl]-2-(2, 4-difluorophenyl)-2-hydroxybutyl]-4-[3,5-dimethyl-4-[(methylamino)acetoxyl benzyl]-1H-1,2,4]triazol-4-ium bromide trifluoroacetic acid salt Physical form: amorphous powder; FAB-MS: m/z 643 (M—Br)+; $^1$H-NMR(CD3OD) δ1.24(3H,d,J=7.3 Hz), 2.21 (6H,s), 2.84(3H,s), 4.30(1H,q,J=7.3 Hz), 4.45(2H,s), 4.65 (1H,d,J=14.2 Hz), 5.11(1H,d,J=14.2 Hz), 5.33(2H,s), 6.76 (1H,m), 7.02(1H,m), 7.14(2H,s), 7.24(1H,m), 7.82(2H,d,J= 8.6 Hz), 8.10(1H,s), 8.18(2H,d,J=8.6 Hz), 8.74(1H,s), 9.99 (1H,s).

Example 24

(2R,3R)-1-[3-[4-(4-Cyanophenyl)thiazol-2-yl l-2-(2, 4-difluorophenyl)-2-hydroxybutyl]-4-[3,5-dimethyl-4-[(propylamino)acetoxylbenzyl]-1H-1,2,4]triazol-4-ium bromide trifluoroacetic acid Physical form: white powder; FAB-MS: m/z 671 (M—Br)+; $^1$H-NMR(CD3OD) δ1.05(3H,t,J=7.4 Hz), 1.25 (3H,d,J=7.3 Hz), 1.77(2H,m), 2.21(6H,s), 3.10(2H,m), 4.31 (1H,q,J=7.4 Hz), 4.47(2H,s), 4.66 (1H,d,J=13.9 Hz), 5.12 (1H,d,J=13.9 Hz), 5.33(2H,s), 6.72–7.29(3H,m), 7.14(2H, s), 7.82(2H,d,J=8.3 Hz), 8.09(1H,s), 8.18(2H,d,J=8.3 Hz), 8.74(1H,s), 10.0(1H,s).

Example 25

1-[(2R,3R)-3-[4-(4-Cyanophenyl)thiazol-2-yl]-2-(2, 4-difluorophenyl)-2-hydroxybutyl]-4-[4-[(S)-2-(methylamino)propionyloxy]-3,5-dimethylbenzyl]-1H-[1,2,4]triazol-4-ium bromide trifluoroacetic acid salt Physical form: white powder; FAB-MS: m/z 657 (M—Br)+; $^1$H-NMR(CD3OD) δ1.25(3H,d,J=7.3 Hz), 1.83

(3H,d,J=7.3 Hz), 2.21(6H,s), 2.83(3H,s), 4.26(1H,q,J=7.3 Hz), 4.57(1H,q,J=7.3 Hz), 4.66(1H,d,J=14.5 Hz), 5.12(1H, d,J=14.5 Hz), 5.34(2H,s), 6.72–7.26(3H,m), 7.15(2H,s), 7.82(2H,d,J=8.6 Hz), 8.11(1H,s), 8.18(2H,d,J=8.6 Hz), 8.75 (1H,s)

Example 26

(2R,3R)-1-[4-[4-(4-cyanophenyl)thiazol-2-yl]-2-(2, 4-difluorophenyl)-2-hydroxy-3-methylbutyl]-4-[3,5-dimethyl-4-[3-(methylamino)propionyloxy]benzyl]-1H-[1,2,4]triazol-4-ium bromide trifluoroacetate Physical form: white powder; FAB-MS: m/z 657 (M-TFA—Br)+; $^1$H-NMR(CD$_3$OD) δ1.24(3H, d, J=6.9 Hz), 2.19(6H, s), 2.78(3H, s), 3.21(2H, t, J=6.6 Hz), 3.42(2H, t, J=6.6 Hz), 4.30(1H, q, J=6.9 Hz), 4.66(1H, d, J=14.2 Hz), 5.11(1H, d, J=14.2 Hz), 5.33(2H, s), 6.73~6.81(1H, m), 6.98~7.07(1H, m), 7.12(2H, s), 7.20–7.30(1H, m), 7.82(2H, d, J=8.7 Hz), 8.10(1H, s), 8.18(2H, d, J=8.7 Hz), 8.73(1H,s), 9.98(1H, s).

Example 27

4-[4-[(S)-2-Amino-3-methylbutanoyloxy]-3,5-dimethylbenzyl]-1-[(2R,3R)-3-[4-(4-cyanophenyl) thiazol-2-yl]-2-(2,4-difluoro-phenyl)-2-hydroxybutyl]-1H-[1,2,4]triazol-4-ium bromide trifluoroacetic acid salt Physical form: white powder; FAB-MS: m/z 671 (M—Br)+; $^1$H-NMR(CD$_3$OD) δ1.21(3H,d,J=6.9 Hz), 1.25 (3H,d,J=6.9 Hz), 1.27(3H,d,J=6.9 Hz), 2.22(6H,s), 2.66(1H, m), 4.27(1H,q,J=6.9 Hz), 4.49(1H,d,J=3.6 Hz), 4.66(1H,d, J=14.2 Hz), 5.12(1H,d,J=14.2 Hz), 5.35(2H,s), 6.73–7.30 (3H,m), 7.15(2H,s), 7.82(2H,d,J=8.6 Hz), 8.10(1H,s), 8.18 (2H,d,J=8.6 Hz), 8.75(1H,s), 10.0(1H,s).

Example 28

(2R,3R)-1-[3-[4-(4-Cyanophenyl)-thiazol-2-yl]-2-(2, 4-difluorophenyl)-2-hydroxy-butyl]-4-[4-[(isopropylamino)acetoxyl-3,5-dimethylbenzyl]-1H-[1,2,4]triazol-4-ium bromide trifluoroacetic acid salt Physical form: amorphous powder; FAB-MS: m/z 671 (M—Br)+; $^1$H-NMR(CD$_3$OD) δ1.24(3H,d,J=6.9 Hz), 1.41 (6H,d,J=6.6 Hz), 2.22(6H,s), 3.32–3.53(1H,m), 4.30(1H,q, J=7.3 Hz), 4.50(2H,s), 4.66(1H,d,J=14.2 Hz), 5.12(1H,d,J= 14.2 Hz), 5.34(2H,s), 6.73–6.78(1H,m), 6.98–7.06(1H,m), 7.15(2H,s), 7.20~7.29(1H,m), 7.82(2H,d,J=8.6 Hz), 8.11 (1H,s), 8.18(2H,d,J=8.6 Hz), 8.74(1H,s).

Example 29

1-[(2R,3R)-3-[4-(4-Cyanophenyl)thiazol-2-yl]-2-(2, 4-difluorophenyl)-2-hydroxybutyl]-4-[(2S)-4-[2-(ethylamino)propionyloxy]-3,5-dimethylbenzyl]-1H-[1,2,4]triazol-4-ium bromide trifluoroacetic acid salt Physical form: amorphous powder; MALDI-TOF-MS: m/z 671 (M—Br)+; $^1$H-NMR(CD$_3$OD) δ1.24(3H,d,J=7.3 Hz), 1.38(3H,t,J=7.3 Hz), 1.83(3H,d,J=7.3 Hz), 2.21(6H,s), 3.14~3.25(2H,m), 4.30(1H,q,J=7.3 Hz), 4.63(1H,q,J=7.3 Hz), 4.66(1H,d,J=14.2 Hz), 5.12(1H,d,J=14.2 Hz), 5.35(2H, s), 6.74~6.80(1H,m), 6.98–7.07(1H,m), 7.16(2H,s), 7.21–7.30(1H,m), 7.82(2H,d,J=8.6 Hz), 8.11(1H,s), 8.18 (2H,d,J=8.6 Hz), 8.75(1H,s), 10.00(1H,s).

Example 30

(2R,3R)-1-[3-[4-(4-Cyanophenyl)-thiazol-2-yl]-2-(2, 4-difluorophenyl)-2-hydroxybutyl]-4-[4-[(ethylamino)acetoxyl-3,5-dimethylbenzyl]-1H-[1,2, 4]triazol-4-ium bromide trifluoroacetic acid salt Physical form: white powder; FAB-MS: m/z 657 (M—Br)+; $^1$H-NMR(CD$_3$OD) δ1.25(3H,d,J=7.3 Hz), 1.38 (3H,t,J=7.3 Hz), 2.22(6H,s), 3.22(2H,q,J=7.3 Hz), 4.27(1H, q,J=7.3 Hz), 4.48(2H,s), 4.67(1H,d,J=14.2 Hz), 5.12(1H,d, J=14.2 Hz), 5.35(2H,s), 6.73–7.29(3H,m), 7.15(2H,s), 7.82 (2H,d,J=8.6 Hz), 8.10(1H,s), 8.18(2H,d,J=8.6 Hz), 8.75(1H, s), 10.0(1H,s).

Example 31

1-[2R,3R)-3-[4-(4-Cyano-phenyl)-thiazol-2-yl]-2-(2, 4-difluoro-phenyl)-2-hydroxybutyl]-4-(3,5-dimethyl-4-methylaminoacetoxy-benzyl)-1H-[1,2,4]triazol-4-ium bromide hydrochloric acid salt 4-[4[(tert-Butoxycarbonyl-methyl-amino)acetoxy]-3,5-dimethyl-benzyl]-1-[2R,3R)-3-[4-(4-cyano-phenyl)-thiazole-2-yl]-2-(2,4-difluoro-phenyl)-2-hydroxy-butyl]-1H-[1,2,4]triazole-4-ium bromide (1:1) was obtained by the similar procedure as described in the method B. To a solution of 4-{4-[(tert-butoxycarbonyl-methyl-amino)-acetoxy]-3,5-dimethylbenzyl}-1-[2R,3R)-3-[4-(4-cyano-phenyl)-thiazole-2-yl]-2-(2,4-difluoro-phenyl)-2-hydroxybutyl]-1H-[1,2,4]triazole-4-ium bromide (1:1) (198.7 g, 241 mmol) in EtOAc (1000 mL), a solution of HCl in EtOAc (4 N, 600 mL) was added at room temperature over a period of 30 min with vigorous stirring. The resulting suspension was stirred at room temperature for 3 h. Precipitates were collected on a glass filter (3G) and washed with ether (500 mL×10) and dried under vacuum at 40° C. for 2 day and then at 80° C. for 12 h to yield 1-[2R,3R)-3-[4-(4-cyanophenyl)-thiazol-2-yl]-2-(2,4-difluoro-phenyl)-2-hydroxy-butyl]-4-(3,5-dimethyl-4-methylaminoacetoxy-benzyl)-1H-[1,2,4]triazol-4-ium bromide hydrochloric acid salt (183.3 g, 100%) as a colorless powder.

Physical form: amorphous powder; FAB-MS: m/z 643 (M—Br)+; 1H-NMR(DMSO-d$_6$) δ1.18 (3H,d,J=7.3 Hz), 2.12(6H,s), 2.64(3H,s), 4.13(1H,q,J=7.3), 4.42(2H,s), 4.72 (1H,d,J=14.2), 5.01(1H,d,J=14.2), 5.39(2H,s), 6.70(1H,s), 6.90–6.94(1H,m), 7.13(2H,m), 7.26–7.34(2H,m), 7.94(2H, d,J=8.3), 8.20(2H,d,J=8.3), 8.44(1H,s), 9.07(1H,s), 9.51 (2H,brs), 10.17(1H,s).

Example 32

The following compounds can be prepared according to a manner similar to Example 1 or 9:

4-(4-Acetoxy-3,5-dimethylbenzyl)-1-[(2R,3R)-2-(2,4-difluorophenyl)-2-hydroxy-3-{5-oxo-4-[4-(2,2,3,3-tetrafluoropropoxy)phenyl]-4,5-dihydro-[1,2,4]triazol-1-yl}butyl]-1H-[1,2,4]triazol-4-ium bromide, 4-(4-acetoxy-3,5-dimethylbenzyl)-1-[(2R)-2-(2,4-difluorophenyl)-2-hydroxy-3-methyl-3-(6-[1,2,4]triazol-1-yl-pyridazin-3-ylsulfanyl)butyl]-1H-[1,2,4]triazol-4-ium bromide, 4-(4-acetoxy-3,5-dimethylbenzyl)-1-[(2R)-2-(2,4-difluorophenyl)-2-hydroxy-3-(3-{(Z)-2-[4-(2,2,3,3-tetrafluoropropoxy)phenyl]vinyl}-[1,2,4]triazol-1-yl) propyl]-1H-[1,2,4]triazol-4-ium bromide, 4-(4-acetoxy-3,5-dimethyl-benzyl)-1-[(2R,3R)-2-(2,4-difluorophenyl)-2-hydroxy-3-methanesulfonylbutyl]-1H-[1,2,4]triazol-4-ium bromide, 4-(4-Acetoxy-3,5-dimethylbenzyl)-1-[(2R-cis)-2-(2,4-difluorophenyl)-4-[4-[4-[1-[(1S,2S)-i -ethyl-2-hydroxypropyl]-5-oxo-1,5-dihydro-[1,2,4]triazol-4-yl] phenyl]piperazin-1-yl]phenoxymethyl]tetrahydrofuran-2-ylmethyl]-1H-[1,2,4]triazol-4-ium bromide, 4-(4-acetoxy-3-methylbenzyl)-1-[(2R-cis)-2-(2,4-difluorophenyl)-4-[4-[4-[1-[(1S,2S)-1-ethyl-2-hydroxypropyl)-5-oxo-1,5-dihydro-[1,2,4]triazol-4-yl]

phenyl]piperazin-1-yl]phenoxymethyl]tetrahydrofuran-2-ylmethyl]-1H-[1,2,4]triazol-4-ium bromide, 4-(4-acetoxybenzyl)-1-[(2R-cis)-2-(2,4-difluorophenyl)-4-[4-[4-[4-[1-[(1S,2S)-1-ethyl-2-hydroxypropyl)-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxy-3,5-dichlorobenzyl)-1-[(2R-cis)-2-(2,4-difluorophenyl)-4-[4-[4-[1-[(1S,2S)-(1-ethyl-2-hydroxypropyl)]-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxy-3-chlorobenzyl)-1-[(2R-cis)-2-(2,4-difluorophenyl)-4-[4-[4-[1-[(1S,2S)-1-ethyl-2-hydroxypropyl)-5-oxo-1,5-dihydro-[1,2,4]triazol-4-yl]phenyl]piperazin-1-yl]phenoxymethyl]tetrahydrofuran-2-ylmethyl]-1H-[1,2,4]triazol-4-ium bromide, 4-(4-acetoxy-3-methylbenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxybenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxy-3,5-dichlorobenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxy-3-chlorobenzyl)-1-[(2R,3R)-2-(2,4-difluorophenyl)-2-hydroxy-3-[4-(4-cyanophenyl)thiazol-2-yl]butyl]-1H-[1,2,4]triazol-4-ium bromide, 4-(4-acetoxy-3,5-dimethylbenzyl)-1-[2-hydroxy-3-methyl-3-methylsulfanyl-2-(4-trifluoromethylphenyl)butyl]-1H-[1,2,4]triazol-4-ium bromide, and 4-(4-acetoxy-3,5-dimethyl-benzyl)-1-[[(5R,6R)-2-methoxyimino-3,3-dimethyl-6-[(4-trifluoromethoxyphenoxy)methyl]cyclohexyl]methyl]-1H-[1,2,4]triazol-4-ium bromide.

Example A

Manufacture of Dry Ampoules for Intramuscular Administration

A lyophilizate of 0.5 g 4-(4-acetoxy-3,5-dimethyl-benzyl)-1-[[(1R,6R)-2-methoxyimino-3,3-dimethyl-6-[(4-trifluoromethoxyphenoxy)methyl]cyclohexyl]methyl]-1H-[1,2,4]triazol-4-ium bromide is prepared in the usual manner and filled into an ampoule. Prior to the administration the lyophilizate is treated with 2.5 ml of a 2% aqueous lidocaine hydrochloride solution.

Example B

Hard gelatin capsules each containing the following ingredients were manufactured in the conventional manner per se:

| | |
|---|---|
| 4-(4-Acetoxy-3,5-dimethyl-benzyl)-1-[[(5R,6R)-2-methoxyimino-3,3-dimethyl-6-[(4-trifluoromethoxyphenoxy)methyl]cyclohexyl]methyl]-1H-[1,2,4]triazol-4-ium bromide | 100 mg |
| Lactose | 56 mg |
| Crystalline Cellulose | 30 mg |
| Silicic acid, Light Anhydrous | 10 mg |
| Talc | 3 mg |
| Magnesium stearate | 1 mg |
| Total | 200 mg |

Example C

Tablets each containing the following ingredients were manufactured in the conventional manner per se:

| | |
|---|---|
| 4-(4-Acetoxy-3,5-dimethyl-benzyl)-1-[[(5R,6R)-2-methoxyimino-3,3-dimethyl-6-[(4-trifluoromethoxyphenoxy)methyl]cyclohexyl]methyl]-1H-[1,2,4]triazol-4-ium bromide | 100 mg |
| Lactose | 60 mg |
| Corn starch | 20 mg |
| Sodium Starch Glycolate | 10 mg |
| Polyvinylpyrrolidone | 6 mg |
| Talc | 3 mg |
| Magnesium stearate | 1 mg |
| Total | 200 mg |

We claim:

1. A compound of the formula:

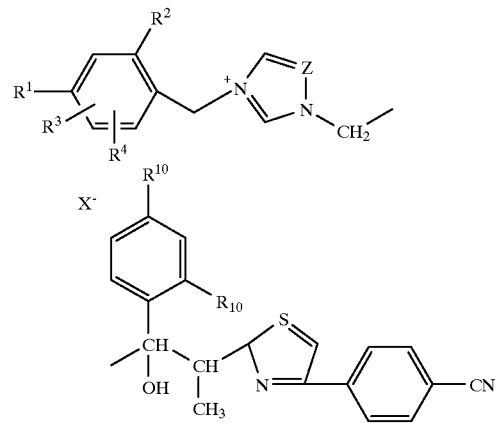

wherein

Z is nitrogen or methine;

$R^1$ and $R^2$ are each independently hydrogen or —OY, wherein Y is selected from the group consisting of formyl, acetyl, propionyl, isobutyryl, pivaloyl, succinoyl, benzoyl, nicotinoyl, phosphoryl, dimethylphosphoryl, aminoacetyl, 3-aminopropionyl, 4-aminobutyryl, (2-amino-acetylamino)-acetyl, (S)-2,5-diaminopentoyl, (S)-2-aminopropionyl, (S)-pyrrolidine-2-carbonyl, (methylamino)acetyl, (propylamino)acetyl, (S)-2-(methylamino) propionyl, 3-(methylamino)propionyl, (S)-2-amino-3-methylbutanoyl, (isopropylamino)acetyl, (2S)-2-(ethylamino)propionyl, and (ethylamino)acetyl;

$R^3$ and $R^4$ are each independently hydrogen, halogen, lower alkyl, lower alkoxy, lower alkylthio, (lower alkylcarbonyl)thiomethyl, carboxy or methoxycarbonyl;

$X^-$ is a pharmaceutically acceptable anion;

$R^{10}$ is a halogen atom;

and pharmaceutically acceptable salts of the compounds, and pharmaceutically acceptable hydrates and solvates thereof.

2. The compound of claim 1 which is 1-[(2R,3R)-3-[4-(4-cyanophenyl)-thiazol-2-yl]-2-(2,4-difluorophenyl)-2-hydroxybutyl]-4-(3,5-dimethyl-4-methylaminoacetoxy-benzyl)-1H-[1,2,4]triazol-4-ium bromide hydrochloric acid salt.

3. The compound of claim 1 which is 1-[(2R,3R)-3-[4-(4-cyanophenyl)-thiazol-2-yl]-2-(2,4-difluorophenyl)-2-hydroxybutyl]-4-(3,5-dimethyl-4-methylaminoacetoxy-benzyl)-1H-[1,2,4]triazol-4-ium bromide hydrobromic acid salt.

4. The compound of claim 1 which is 1-[(2R,3R)-3-[4-(4-cyanophenyl)-thiazol-2-yl]-2-(2,4-difluorophenyl)-2-hydroxybutyl]-4-(3,5-dimethyl-4-methylaminoacetoxybenzyl)-1H-[1,2,4]triazol-4-ium chloride hydrochloric acid salt.

5. The compound of claim 1 which is (2R,3R)-1-[3-[4-(4-cyanophenyl)-thiazol-2-yl]-2-(2,4-difluorophenyl)-2-hydroxybutyl]-4-[4-[(ethylamino)acetoxy]-3,5-dimethylbenzyl]-1H-[1,2,4]triazol-4-ium bromide trifluoroacetic acid salt.

6. The compound of claim 1 which is 1-[(2R,3R)-3-[4-(4-cyanophenyl)-thiazol-2-yl]-2-(2,4-difluorophenyl)-2-hydroxybutyl]-4-[(2S)-4-[2(ethylamino)propionyloxy]-3,5-dimethyl-benzyl]-1H-[1,2,4]triazol-4-ium bromide trifluoroacetic acid salt.

7. The compound of claim 1 which is (2R,3R)-1-[3-[4-(4-cyanophenyl)-thiazol-2-yl]-2-(2,4-difluorophenyl)-2-hydroxybutyl]-4-[4-[(isopropylamino)acetoxy]-3,5-dimethylbenzyl)-1H-[1,2,4]triazol-4-ium bromide trifluoroacetic acid salt.

8. The compound of claim 1 which is 4-[4-[(S)-2-amino-methyl-butanoyloxy]-3,5-dimethylbenzyl]-1-[(2R,3R)-3-[4-(4-cyanophenyl)-thiazol-2-yl]-2-(2,4-difluorophenyl)-2-hydroxybutyl]-1H-[1,2,4]triazol-4-ium bromide trifluoroacetic acid salt.

9. The compound of claim 1 which is (2R,3R)-1-[4-[4-(4-cyanophenyl)-thiazol-2-yl]-2-(2,4-difluorophenyl)-2-hydroxy-3-methyl-butyl]-4-(3,5-dimethyl-4-[3-(methylamino)-propionyloxy]benzyl)-1H-[1,2,4]triazol-4-ium bromide trifluoroacete.

10. The compound of claim 1 which is 1-[(2R,3R)-3-[4-(4-cyanophenyl)-thiazol-2-yl]-2-(2,4-difluorophenyl)-2-hydroxybutyl]-4-[4-[(S)-2-(methylamino)-propionyloxy]-3,5-dimethylbenzyl]-1H-[1,2,4]triazol-4-ium bromide trifluoroacetic acid salt.

11. The compound of claim 1 which is (2R,3R)-1-[3-[4-(4-cyanophenyl)-thiazol-2-yl]-2-(2,4-difluorophenyl)-2-hydroxybutyl]-4-[3,5-dimethyl-4-[(propylamino)acetoxy]benzyl]-1H-[1,2,4]triazol-4-ium bromide trifluoroacetic acid salt.

12. The compound of claim 1 which is 1-[(2R,3R)-[3-[4-(4-cyanophenyl)-thiazol-2-yl]-2-(2,4-difluorophenyl)-2-hydroxybutyl]-4-[3,5-dimethyl-4-[(methylamino)acetoxy]benzyl]-1H-[1,2,4]triazol-4-ium bromide trifluoroacetic acid salt.

13. The compound of claim 1 which is 4-[4-[(S)-(2-amino-propionyloxy)-3,5-dimethylbenzyl]-1-[(2R,3R)-3-[4-(4-cyanophenyl)-thiazol-2-yl]-2-(2,4-difluorophenyl)-2-hydroxy-butyl]-1H-[1,2,4]triazol-4-ium bromide trifluoroacetic acid salt.

14. The compound of claim 1 which is 1-[(2R,3R)-3-[4-(4-cyanophenyl)-thiazol-2-yl]-2-(2,4-difluorophenyl)-2-hydroxy-butyl]-4-[4-[(S)-2,5-diaminopentoyloxy]-3,5-dimethyl-benzyl]-1H-[1,2,4]triazol-4-ium bromide trifluoroacetic acid salt.

15. The compound of claim 1 which is (2R,3R)-4-[4-[[2(aminoacetyl)amino]acetoxy]-3,5-dimethylbenzyl]-1-[3-[4-(4-cyanophenyl)-thiazol-2-yl]-2-(2,4-difluorophenyl)-2-hydroxybutyl]-1H-[1,2,4]triazol-4-ium bromide trifluoroacetic acid salt.

16. The compound of claim 1 which is (2R,3R)-4-[4-(4-amino-butyryloxy)-3,5-dimethylbenzyl]-1-[4-[4-(4-cyanophenyl)-thiazol-2-yl]-2-(2,4-difluorophenyl)-2-hydroxy-3-methylbutyl]-1H-[1,2,4]triazol-4-ium bromide trifluoroacetic acid salt.

17. The compound of claim 1 which is (2R,3R)-4-[4-(3-aminopropionyloxy)-3,5-dimethylbenzyl]-1-[4-[4-(4-cyanophenyl)-thiazol-2-yl]-2-(2,4-difluorophenyl)-2-hydroxy-3-methylbutyl]-1H-[1,2,4]triazol-4-ium bromide trifluoroacetic acid salt.

18. The compound of claim 1 which is (2R,3R)-4-(4-aminoacetoxy-3,5-dimethylbenzyl)-1-[3-[4-(4-cyanophenyl)-thiazol-2-yl]-2-(2,4-difluorophenyl)-2-hydroxybutyl]-1H-[1,2,4]triazol-4-ium bromide trifluoroacetic acid salt.

19. The compound of claim 1 which is 1-[(2R,3R)-3-[4-(4-cyanophenyl)-thiazol-2-yl]-2-(2,4-difluorophenyl)-2-hydroxy-butyl]-4-[(S)-3,5-dimethyl-4-(pyrrolidine-2-carbonyloxy)-benzyl]-1H-[1,2,4]triazol-4-ium bromide trifluoroacetic acid salt.

20. The compound of claim 1 which is (2R,3R)-4-(4-aminoacetoxy-2-carboxybenzyl)-1-[3-[4-(4-cyanophenyl)-thiazol-2-yl]-2-(2,4-difluorophenyl)-2-hydroxybutyl]-1H-[1,2,4]triazol-4-ium bromide trifluoroacetic acid salt.

* * * * *

UNITED STATES PATENT AND TRADEMARK OFFICE
CERTIFICATE OF CORRECTION

PATENT NO. : 5,900,486

DATED : May 4, 1999

INVENTOR(S) : Shigeyasu Ichihara, et al.

It is certified that error appears in the above-identified patent and that said Letters Patent is hereby corrected as shown below:

Column 22, line 55, delete "and" and insert --or a--.

Column 22, line 55, change "salts" to --salt--.

Column 22, line 55, change "compounds" to --compound--.

Column 22, line 56, delete "and" and insert --or a--.

Column 22, line 56, delete "hydrates and solvates" and insert --hydrate or solvate--

Signed and Sealed this

Second Day of November, 1999

Q. TODD DICKINSON

Attest:

Attesting Officer

Acting Commissioner of Patents and Trademarks